United States Patent
Wiederin et al.

(10) Patent No.: US 9,909,957 B1
(45) Date of Patent: Mar. 6, 2018

(54) INTRODUCING HYDROGEN GAS TO AN ICP INSTRUMENT FOR ENHANCED DETECTION OF LOW-SENSITIVITY ELEMENTS

(71) Applicant: Elemental Scientific, Inc., Omaha, NE (US)

(72) Inventors: Daniel R. Wiederin, Omaha, NE (US); Austin Schultz, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 689 days.

(21) Appl. No.: 13/729,323

(22) Filed: Dec. 28, 2012

Related U.S. Application Data

(60) Provisional application No. 61/581,761, filed on Dec. 30, 2011, provisional application No. 61/584,571, filed on Jan. 9, 2012.

(51) Int. Cl.
  *G01N 1/28* (2006.01)
  *B01D 19/00* (2006.01)

(52) U.S. Cl.
  CPC ........... *G01N 1/28* (2013.01); *B01D 19/0005* (2013.01)

(58) Field of Classification Search
  CPC .............................. G01N 1/28; B01D 19/0005
  USPC .......................................... 436/181; 73/61.42
  See application file for complete search history.

(56) References Cited

U.S. PATENT DOCUMENTS

| | | | | |
|---|---|---|---|---|
| 5,792,663 A | * | 8/1998 | Fry ........................... | B01D 1/22 159/13.1 |
| 6,122,050 A | * | 9/2000 | Rutzke ..................... | G01J 3/443 356/316 |

OTHER PUBLICATIONS

Marco Grotti, Cristina Lagomarsino and Jean Michel Mermet "Effect of operating conditions on excitation temperature and electron No. density in axially-viewed ICP-OES with introduction of vapours or aerosols" J. Anal. At. Spectrom., 2006, 21, 963-969.*
P. Heitland and J. A. C. Broekaert "Addition of Small Amounts of Helium and Hydrogen to the Working Gases in Slurry Nebulization Inductively Coupled Plasma Atomic Emission Spectrometry for the Analysis of Ceramic Powders" Journal of Analytical Atomic Spectrometry, Sep. 1997, vol. 12 (981-986).*
P. Schramel and Li-Qiang Xu "Determination of arsenic, antimony, bismuth, selenium and tin in biological and environmental samples by continuous flow hydride generation ICP-AES without gas-liquid separator" Fresenius J Anal Chem (1991) 340:41-47.*
Pending U.S. Appl. No. 13/560,198, filed Jul. 27, 2012.

* cited by examiner

*Primary Examiner* — Christopher Adam Hixson
*Assistant Examiner* — Emily R. Berkeley
(74) *Attorney, Agent, or Firm* — Advent, LLP

(57) ABSTRACT

A method for detecting material in a sample using an ICP instrument includes preparing the sample for analysis by the ICP instrument using hydrogen gas. For example, hydrogen gas can be generated by initiating a hydride generation reaction with the sample. Further, hydrogen gas can be introduced to a component part of the sample. For instance, hydrogen gas can be added to an injector gas in a spray chamber of the ICP instrument.

6 Claims, 10 Drawing Sheets

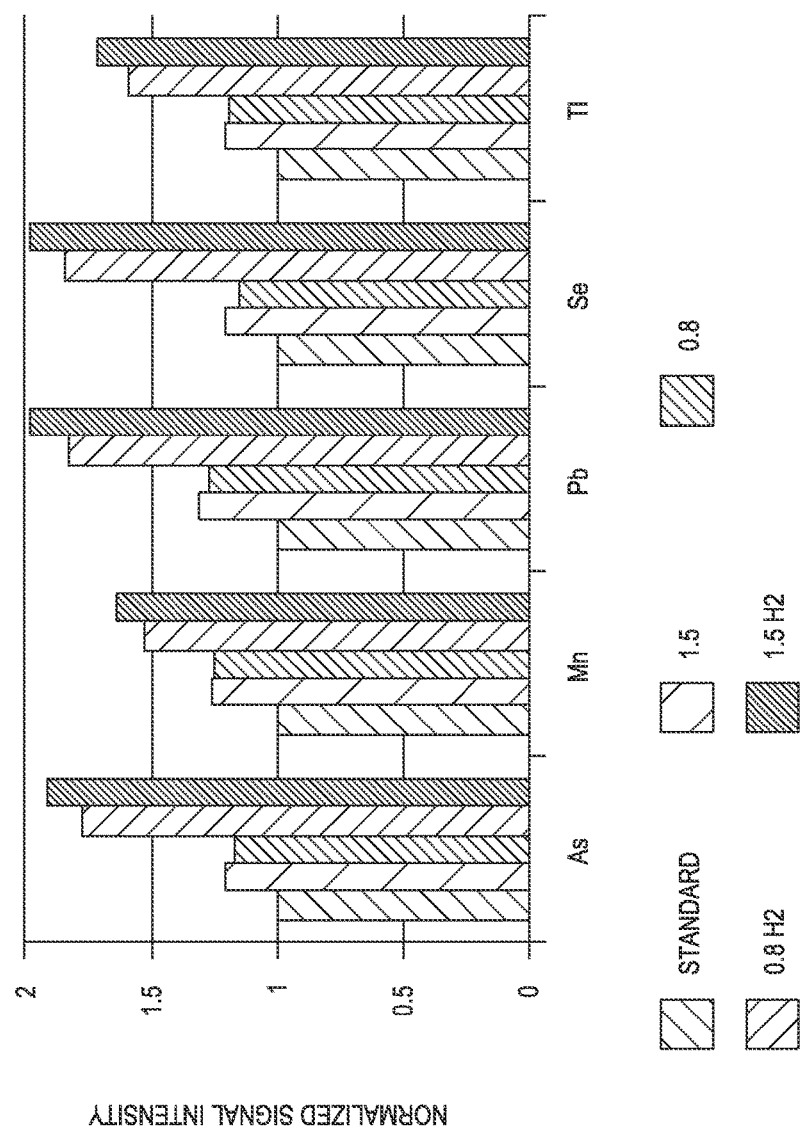

INTRODUCING HYDROGEN GAS TO AN ICP INSTRUMENT FOR ENHANCED DETECTION OF LOW-SENSITIVITY ELEMENTS

CROSS-REFERENCE TO RELATED APPLICATIONS

The present application claims the benefit under 35 U.S.C. § 119(e) of U.S. Provisional Application Ser. No. 61/581,761, filed Dec. 30, 2012, and titled "INTRODUCING HYDROGEN GAS TO AN ICP INSTRUMENT FOR ENHANCED DETECTION OF LOW-SENSITIVITY ELEMENTS" and U.S. Provisional Application Ser. No. 61/584,571, filed Jan. 9, 2012, and titled "INTRODUCING HYDROGEN GAS TO AN ICP INSTRUMENT FOR ENHANCED DETECTION OF LOW-SENSITIVITY ELEMENTS." U. S. Provisional Application Ser. Nos. 61/581,761 and 61/584,571 are herein incorporated by reference in their entireties.

BACKGROUND

Spectrometry refers to the measurement of radiation intensity as a function of wavelength to identify component parts of materials. Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample. The sample to be analyzed is often provided in a sample mixture.

Sample introduction systems may be employed to introduce liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A method for detecting material in a sample using an ICP instrument is described. The sample is prepared for analysis by the ICP instrument using hydrogen gas. For example, hydrogen gas can be generated by initiating a hydride generation reaction with the sample. Further, hydrogen gas can be introduced to a component part of the sample. For instance, hydrogen gas can be added to an injector gas in a spray chamber of the ICP instrument. A fractional-volatilization separator configured to separate a sample mixture into its component parts (fractions) is also described. In one or more implementations, the fractional-volatilization separator includes a liquid inlet port for receiving a liquid mixture containing a first component part (e.g., hydrogen gas) and a second component part. The fractional-volatilization separator comprises an interior wall portion configured to cause the liquid mixture introduced at the liquid inlet port to flow from the liquid inlet port, evenly distribute (spread) across the interior wall portion, and flow to a liquid waste outlet port. The evaporation of a component part from the liquid mixture is enhanced by increasing the surface area of the liquid mixture as it spreads across the interior wall portion of the separator body in the presence of the carrier gas.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 9 is a graph illustrating improvements in signal intensity when hydrogen gas is added to ICP instrumentation in accordance with example implementations of the present disclosure.

DETAILED DESCRIPTION

Overview

Axially-viewed Inductively Coupled Plasma (ICP) spectrometry is a technique that uses horizontal or "end-on" ICP instrumentation to detect and/or quantify components of a sample. Radially-viewed ICP spectrometry uses vertical or "side-on" plasmas. The sample to be analyzed is typically provided in the form of a sample mixture. Fractional-volatilization separation may be used to separate a more volatile component from a less volatile component of a sample material. This may be desirable when it is necessary to detect a small amount of a component in a material mixture. For example, fractional-volatilization can be used to separate hydrides from a liquid component of a sample material. The hydrides can be generated with, for instance, a hydride generation reaction. In many instances, it may be difficult to detect certain materials using ICP techniques. For example, it may be particularly difficult to detect the presence of elements such as arsenic (As), selenium (Se), lead (Pb), and/or thallium (Tl) using ICP instruments.

Accordingly, the present disclosure is directed to a method for detecting material in a sample using an ICP instrument, where the sample is prepared for analysis by the ICP instrument using hydrogen gas ($H_2$). For example, hydrogen gas can be generated by initiating a hydride generation reaction with the sample. Further, hydrogen gas can be introduced to a component part of the sample. For instance, hydrogen gas can be added to an injector gas in a spray chamber of the ICP instrument. A fractional-volatilization Gas-Liquid Separator (GLS) is also described that may be easily manufactured from blown quartz, or the like. The fractional-volatilization separator may be suitable for use in a system for performing hydride generation (e.g., for mass spectrometry).

In the following discussion, example implementations of techniques for enhancing the sensitivity of ICP instruments by introducing hydrogen gas to a sample are first described.

Example Implementations

Figure 1:
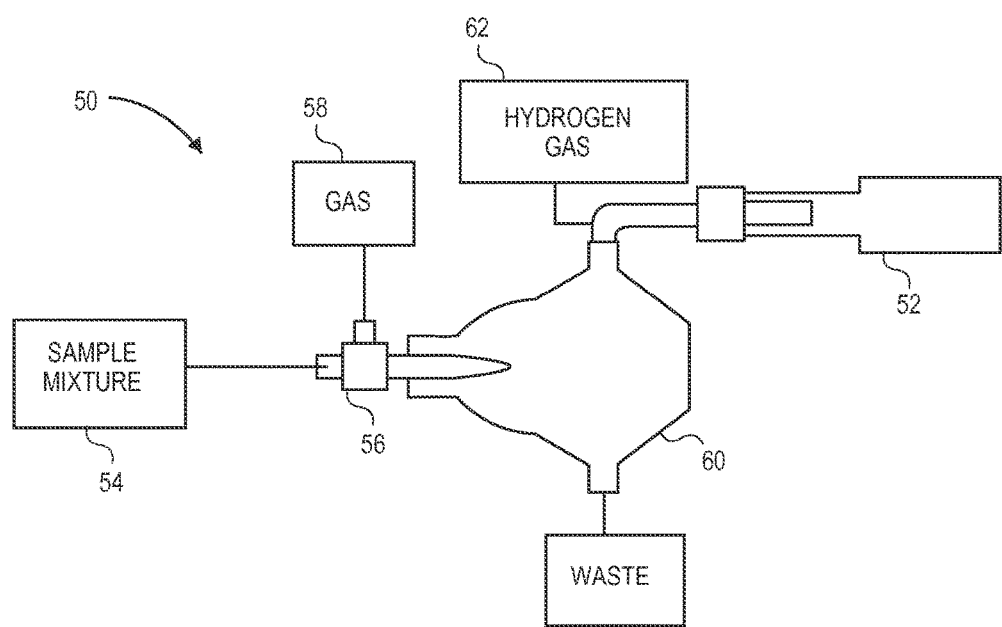
FIG. 1 is a diagrammatic illustration of a system for enhancing the sensitivity of an ICP instrument by adding hydrogen gas to a sample in a spray chamber.

FIG. 1 illustrates a system 50 for enhancing the sensitivity of an ICP instrument by adding hydrogen gas to a sample in accordance with example implementations of the present disclosure. In implementations, a sample can be provided to an IPC torch 52 by forming an aerosol from a sample mixture 54 using, for instance, a nebulizer 56. In some implementations, the aerosol may be a wet aerosol, while in other implementations, the aerosol may be a dry aerosol. A gas 58, such as an injector gas, a sample gas, a carrier gas, and so forth, may also be provided to the ICP torch 52. The aerosolized sample and/or the gas 58 may be supplied to the ICP torch 52 using a spray chamber 60. Hydrogen gas 62 is added to the sample to enhance the sensitivity of the ICP instrumentation. For example, hydrogen gas 62 can be introduced to the sample in the spray chamber 60. The introduction of the hydrogen gas 62 can significantly increase the sensitivity of ICP instruments, which can allow for the detection of elements such as As, Se, Pb, and Tl, as well as other low-sensitivity elements, among other materials. Thus, techniques in accordance with the present disclosure can be useful for meeting current and future regulatory detection limits for low-sensitivity elements.

Figure 2A:
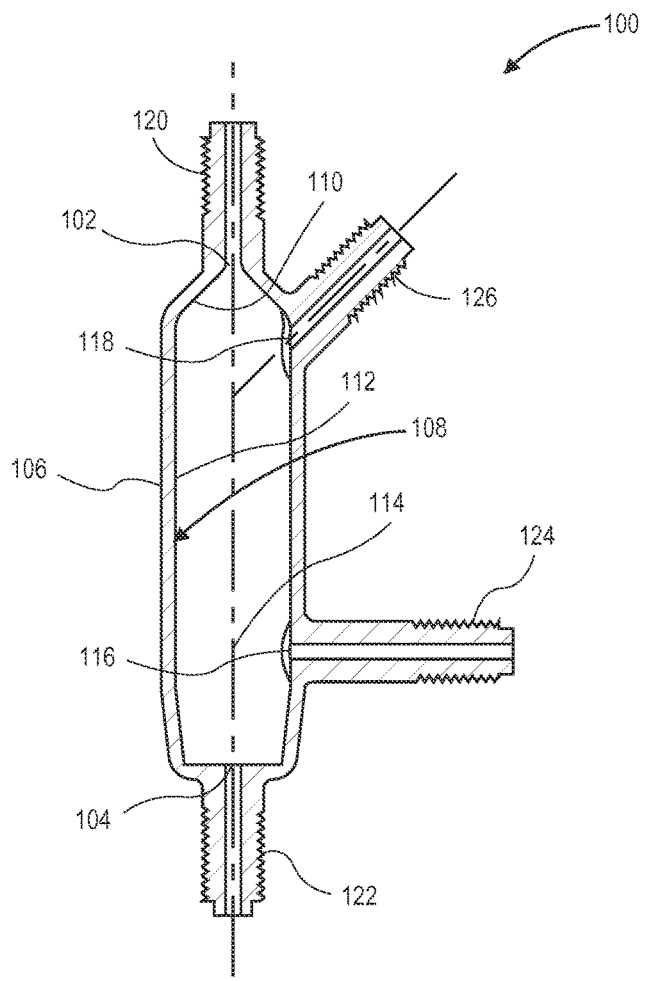
FIG. 2A is a cross-sectional side elevation view of a fractional-volatilization separator in accordance with an example implementation of the present disclosure.
Figure 2B:
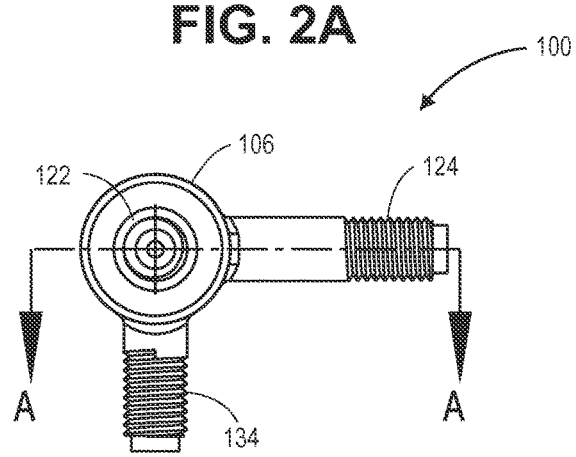
FIG. 2B is a bottom plan view of the fractional-volatilization separator illustrated in FIG. 1, where section line A-A indicates the direction of the cross-section of FIG. 1.
Figure 3:
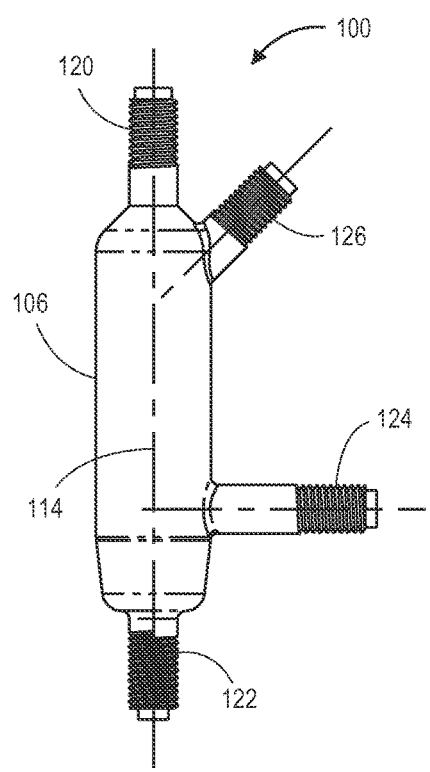
FIG. 3 is a side elevation view of the fractional-volatilization separator illustrated in FIG. 1.
Figure 4:
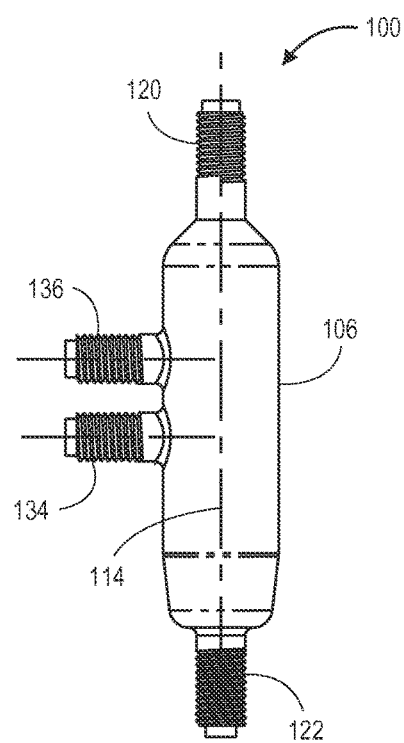
FIG. 4 is a front elevation view of the fractional-volatilization separator illustrated in FIG. 1.
Figure 5:
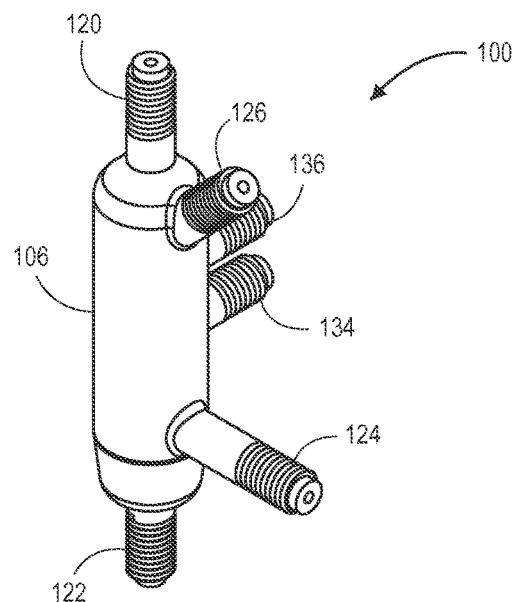
FIG. 5 is an isometric view of the fractional-volatilization separator illustrated in FIG. 1.
Figure 6A:
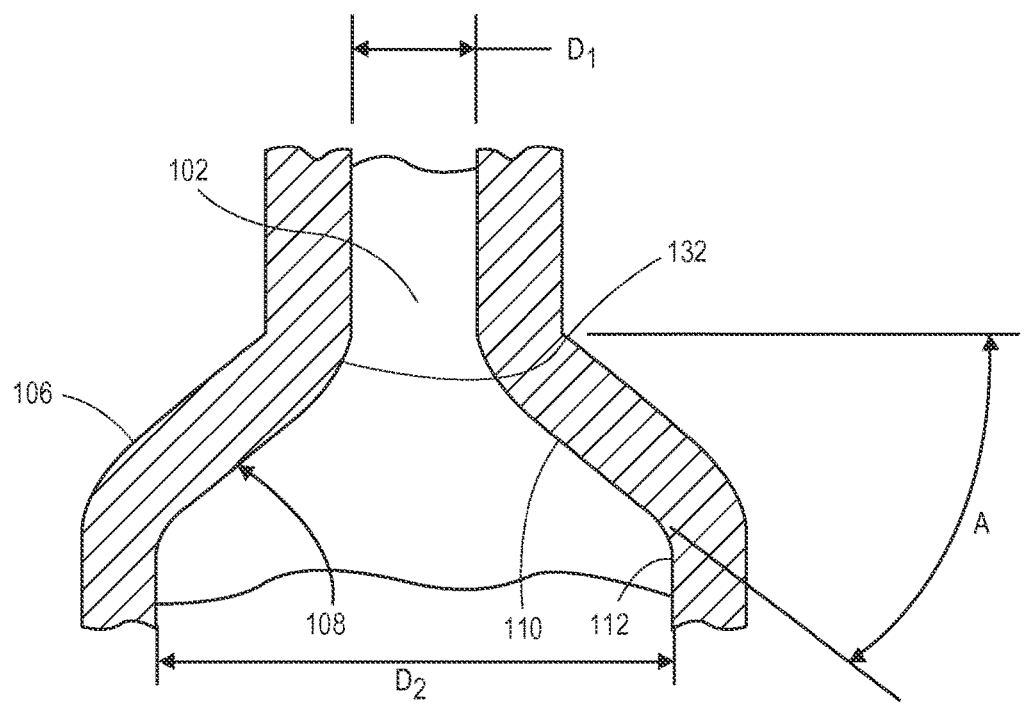
FIG. 6A is a partial cross-sectional side elevation view of the fractional-volatilization separator illustrated in FIG. 1.
Figure 6B:
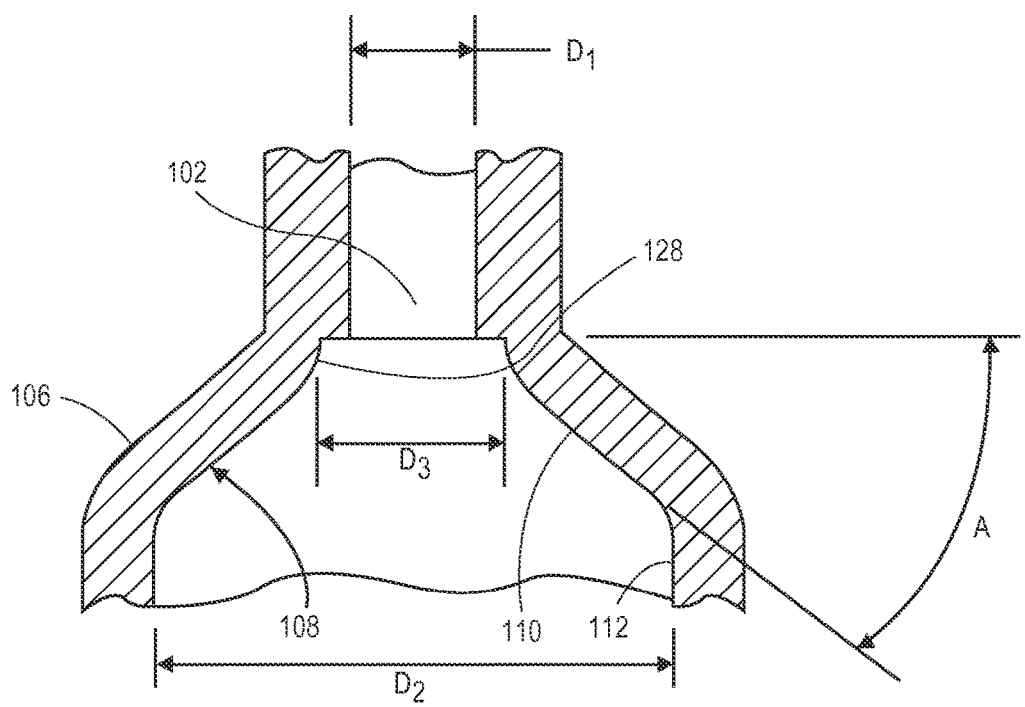
FIG. 6B is a partial cross-sectional side elevation view illustrating another fractional-volatilization separator in accordance with an example implementation of the present disclosure.
Figure 6C:
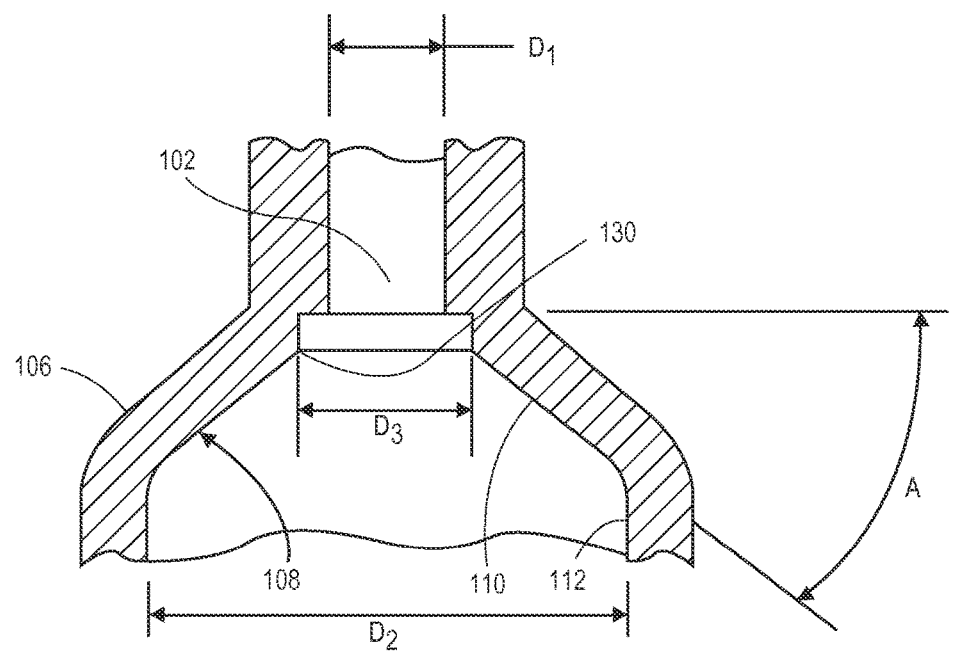
FIG. 6C is a partial cross-sectional side elevation view illustrating a further fractional-volatilization separator in accordance with an example implementation of the present disclosure.
Figure 6D:
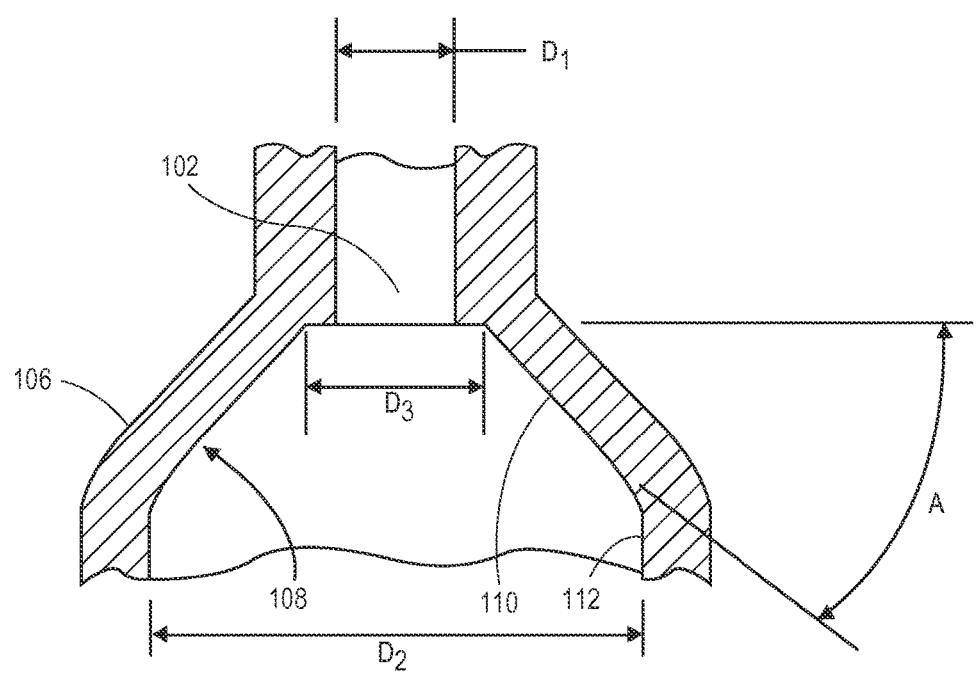
FIG. 6D is a partial cross-sectional side elevation view illustrating another fractional-volatilization separator in accordance with an example implementation of the present disclosure.
Figure 7:
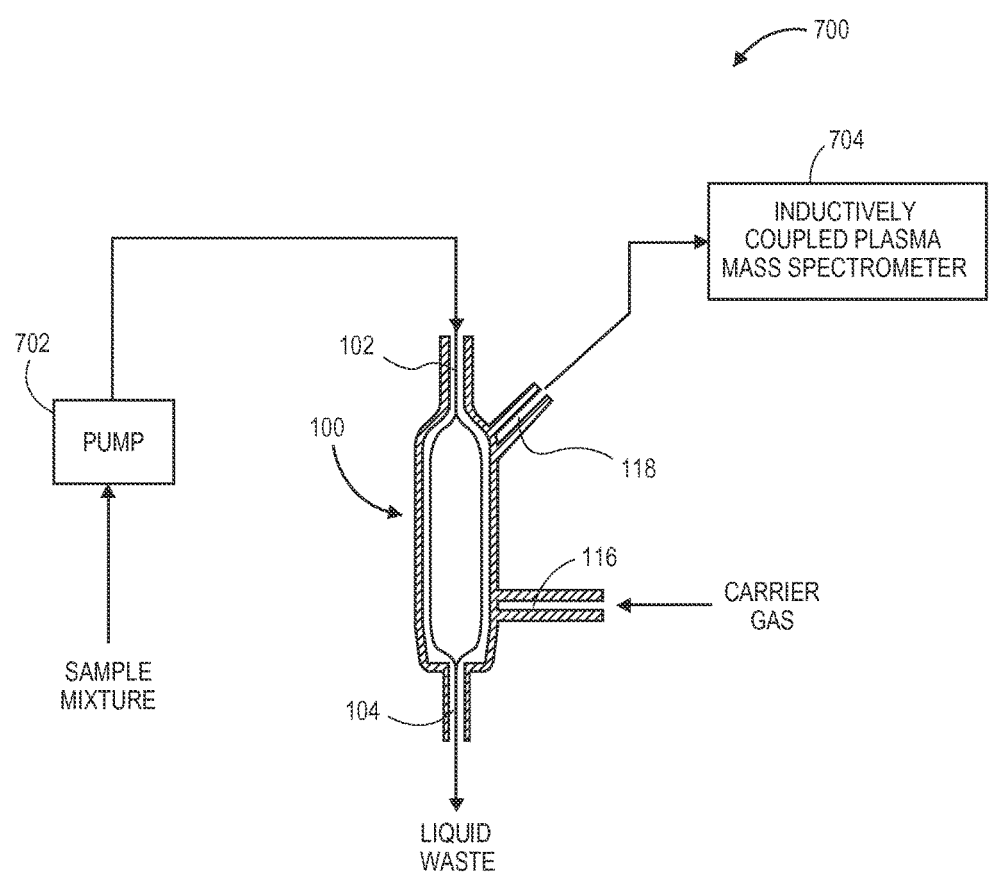
FIG. 7 is a schematic illustrating a mass spectrometer system utilizing a fractional-volatilization separator in accordance with an example implementation of the present disclosure.

FIGS. 2A through 6D illustrate a fractional-volatilization separator 100 in accordance with example implementations of the present disclosure. As shown, the fractional-volatilization separator 100 includes a liquid inlet port 102 for receiving a liquid mixture. In implementations, the liquid mixture may include various formulations of liquid and possibly gas components. For example, the liquid mixture may comprise a mixture of liquid and gas, two or more liquids having different vapor pressures, and other component combinations. In implementations, the liquid mixture comprises a mixture of a liquid and hydrogen gas. The mixture may also comprise a hydride. However, the liquid mixture does not necessarily comprise a mixture of a liquid and hydrogen gas. For instance, the mixture may comprise a mixture of liquid and a hydride, e.g., where hydrogen gas has been separated from the mixture. The mixture may also comprise a mixture of a liquid and a non-hydride, non-hydrogen gas. When the fractional-volatilization separator 100 is oriented in a substantially vertical upright position (e.g., as illustrated in FIG. 2A), the liquid inlet port 102 is oriented at or near the top of the fractional-volatilization separator 100. The fractional-volatilization separator 100 also includes a liquid waste outlet port 104 for draining the liquid mixture (e.g., after a first component part has been separated from a second component part of the liquid mixture). When the fractional-volatilization separator 100 is oriented in the upright position, the liquid waste outlet port 104 is oriented at or near the bottom of the fractional-volatilization separator 100.

The fractional-volatilization separator 100 includes a separator body 106 having an interior wall portion 108 connecting the liquid inlet port 102 and the liquid waste outlet port 104. In implementations, the interior wall portion 108 defines a generally longitudinal interior cavity having a first region 110 adjacent to the liquid inlet port 102 and a second region 112 adjacent to the liquid waste outlet port 104. For example, the generally longitudinal interior cavity may extend generally along a longitudinal axis 114 of the separator body 106. In implementations, the generally longitudinal interior cavity of the separator body 106 is configured so that a liquid mixture introduced at the liquid inlet port 102 will be evenly distributed/spread across the interior wall portion 108 and flow to the liquid waste outlet port 104.

The fractional-volatilization separator 100 includes a carrier gas inlet port 116 for receiving a carrier gas, or the like. The carrier gas inlet port 116 is connected to the separator body 106 for fluid communication with the generally longitudinal interior cavity of the separator body 106. In some implementations, when the fractional-volatilization separator 100 is oriented in the upright position illustrated in FIG. 2A, the carrier gas inlet port 116 is oriented at or near the bottom of the fractional-volatilization separator 100. For example, the carrier gas inlet port 116 may be connected to the separator body 106 at or near the liquid waste outlet port 104. However, in other implementations, the carrier gas inlet port 116 may be connected to the separator body 106 in other orientations, such as positioned near the liquid inlet port 102. The fractional-volatilization separator 100 includes a carrier gas outlet port 118 for expelling the carrier gas. The carrier gas outlet port 118 is also connected to the separator body 106 for fluid communication with the generally longitudinal interior cavity of the separator body 106. In some implementations, when the fractional-volatilization separator 100 is oriented in the upright position, as illustrated in FIG. 2A, the carrier gas outlet port 118 is oriented near the top of the fractional-volatilization separator 100. For example, the carrier gas outlet port 118 may be connected to the separator body 106 near the liquid inlet port 102. In other implementations, the carrier gas outlet port 118 may be connected to the separator body 106 in other orientations, such as positioned near the liquid waste outlet port 104.

In implementations, the carrier gas outlet port 118 may be oriented upwardly at an angle from the horizontal (e.g., for preventing liquid waste from the liquid mixture from entering the stream of carrier gas expelled at the carrier gas outlet port 118). For example, the carrier gas outlet port 118 may be oriented upwardly at an angle of approximately forty-five degrees (45°) from the horizontal. However, this angle is provided by way of example only, and it should be noted that the carrier gas outlet port 118 may be oriented at a number of different angles. In some implementations, the liquid inlet port 102, the liquid waste outlet port 104, the separator body 106, the carrier gas inlet port 116, and the carrier gas outlet port 118 may be glass blown from quartz. Further, the interior wall portion 108 may be frosted in this type of implementation to enhance the evaporation of components of the liquid mixture into the carrier gas by increasing the surface area of the interior wall portion 108. In other implementations, the fractional-volatilization separator 100 may be constructed from other materials. For example, the liquid inlet port 102, the liquid waste outlet port 104, the separator body 106, the carrier gas inlet port 116, and the carrier gas outlet port 118 may be formed from glass, polyether ether ketone (PEEK), Lexan polycarbonate acrylic, and various mixtures of plastic and other compounds, such as plastic and hydrofluoric acid. However, this list is provided by way of example and is not meant to be restrictive of the present disclosure. Thus, other materials may be used to construct the fractional-volatilization separator 100.

In example implementations, the liquid inlet port 102 may extend through a coupling 120. The coupling 120 may be connectable to a source of liquid mixture, such as a liquid supply tube having a threaded connecter, or the like. In implementations, the coupling 120 may include threads for connecting with a threaded connector. In other implementations, the coupling 120 may include other connecting features, such as quick connect coupling hardware, or the like. The liquid waste outlet port 104 may extend through a coupling 122, while the carrier gas inlet port 116 may extend through a coupling 124, and the carrier gas outlet port 118 may extend through a coupling 126. The couplings 122, 124, and/or 126 may be configured in a similar manner to the coupling 120. For example, the coupling 122 may include threads for connecting to a threaded connector of a tube for receiving the liquid mixture. The coupling 124 may include threads for connecting to a threaded connector of a tube for supplying the carrier gas, while the coupling 126 may include threads for connecting to a threaded connector of a tube for receiving the carrier gas.

Referring now to FIGS. 6A through 6D, the liquid inlet port 102 defines an aperture having a first diameter $D_1$. The second region 112 of the interior wall portion 108 has a second diameter $D_2$. In implementations, the first region 110 of the interior wall portion 108 transitions from the first diameter $D_1$ of the liquid inlet port 102 to the second diameter $D_2$ of the interior wall portion 108. The first interior wall portion 108 is configured to cause a liquid mixture introduced at the liquid inlet port 102 to flow from the liquid inlet port 102, spread across the interior wall portion 108, and collect at the liquid waste outlet port 104 when the generally longitudinal interior cavity is oriented in an upright position. Thus, the configuration of the interior wall portion 108 is designed to enhance evaporation of a first component part from a second component part of a liquid mixture as a carrier gas flows from the carrier gas inlet port 116 to the carrier gas outlet port 118 across the mixture.

The evaporation of the first component part from the liquid mixture is enhanced by increasing the surface area of the liquid mixture as it coats the interior wall portion 108 in the presence of the carrier gas. Thus, the interior wall portion 108 is constructed to cause the liquid mixture introduced at the liquid inlet port 102 to adhere to the interior wall portion 108. For example, the first region 110 of the interior wall portion 108 may be oriented at an angle A from the horizontal, as illustrated in FIGS. 6A through 6D. In some implementations, angle A may be approximately forty-five degrees (45°). However, in other implementations, different angles may be employed. For instance, angle A may be between at least approximately thirty degrees (30°) and at least approximately sixty degrees (60°).

In an implementation described in FIG. 6A, the first diameter $D_1$ may transition to the second diameter $D_2$ via a curved transition 132. In the implementations described in FIGS. 6B through 6D, the first region 110 transitions from the first diameter $D_1$ to a third diameter $D_3$ across a substantially horizontal plane, and then from the third diameter $D_3$ to the second diameter $D_2$. In the implementation described in FIG. 6B, the cross-sectional profile of the interior wall portion 108 includes a curved transition 128 from the third diameter $D_3$ to the second diameter $D_2$. In another implementation described in FIG. 6C, the cross-sectional profile of the interior wall portion 108 includes an angled transition 130 from the third diameter $D_3$ to the second diameter $D_2$. The cross-sectional profile may also transition directly from the third diameter $D_3$ to the second diameter $D_2$, as illustrated in FIG. 6D. In other implementations, the first diameter $D_1$ may transition to the second diameter $D_2$ along different cross-sectional geometries. The transitions described in the accompanying figures are provided by way of example only and are not meant to be restrictive. Thus, other transition profiles may be employed having other various shapes for causing the liquid mixture to spread across the interior wall portion 108, including convex curves, concave curves, angled transitions and the like.

The fractional-volatilization separator 100 may include a mounting structure for mounting the separator 100 to a supporting structure, such as a support stand or housing. For example, in the implementation shown, the fractional-volatilization separator 100 is illustrated as including a first support attachment point 134 and possibly a second support attachment point 136 connected to the separator body 106 for supporting the separator body 106. In implementations, the first support attachment point 134 and/or the second support attachment point 136 may be threaded for connecting to threaded support structures. In other implementations, the first support attachment point 134 and/or the second support attachment point 136 may include other connecting features, such as quick connect coupling hardware, or the like.

FIG. 7 illustrates a system 700 in accordance with example implementations of the present disclosure for detecting one or more components in a liquid mixture. As shown, the system 700 includes a fractional-volatilization separator 100 having a liquid inlet port 102 for receiving a sample mixture, a liquid waste outlet port 104 for draining the sample mixture, a carrier gas inlet port 116 for receiving a carrier gas, and a carrier gas outlet port 118 for expelling the carrier gas, where the sample mixture is distributed across an interior wall portion connecting the liquid inlet port 102 and the liquid waste outlet port 104 in the presence of the carrier gas (e.g., as previously described). The fractional-volatilization separator 100 may be connected to a pump 702 (e.g., a peristaltic pump) for pumping the sample mixture to the liquid inlet port 102. The fractional-volatilization separator 100 may also be connected to a mass spectrometer, such as an axially-viewed ICP instrument (e.g., inductively coupled plasma mass spectrometer (ICP-MS) 704, or the like).

In implementations, the system 700 may be employed to detect hydride forming elements, such as As, Se, and/or antimony (Sb). For example, hydrides from a sample mixture may be separated from liquid waste, and then carried to an ICP-MS 704 injector in gaseous form with the carrier gas, where the hydrides may be detected. In implementations, hydrogen gas may also be generated using a hydride generation reaction with a sample, along with a hydride. In other implementations, hydrogen gas may be supplied to an ICP instrument separately, such as by introducing hydrogen gas to the center channel of an ICP instrument. As previously noted, the introduction of hydrogen gas can significantly increase the sensitivity of an ICP instrument. The expelled carrier gas may be supplied to a spray chamber and/or a torch. In example implementations, the carrier gas may be Argon (Ar). However, it is should be noted that the above-referenced hydride forming elements, and/or carrier gas are provided by way of example only, and are not meant to be restrictive of the present disclosure. Thus, other various mixtures and components may be used with the system 700, including other hydride forming compounds, and the like.

Figure 8:
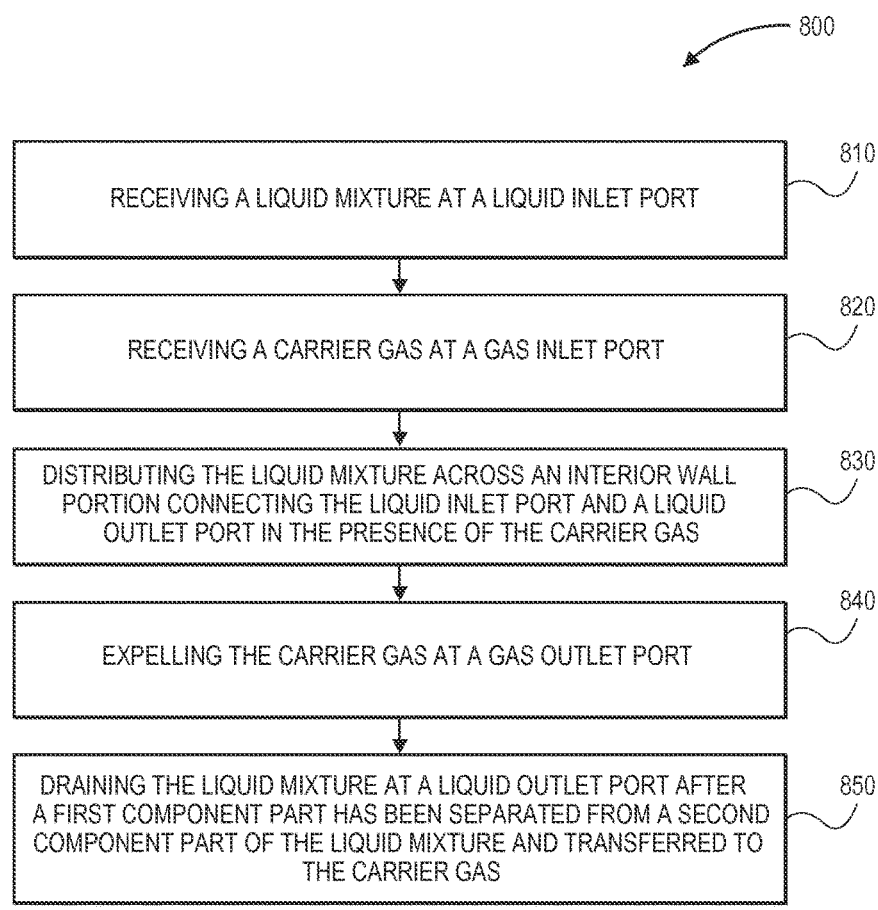
FIG. 8 is a flow diagram illustrating a method for separating a first component part from a second component part of a liquid mixture in accordance with an example implementation of the present disclosure, where the mixture is spread across an interior wall portion of a fractional-volatilization separator body in the presence of a carrier gas.

Referring now to FIG. 8, a method 800 for separating a first component part from a second component part of a liquid mixture is described. In accordance with the method 800, a liquid mixture is received at a liquid inlet port (Block 810). A carrier gas is received at a carrier gas inlet port (Block 820). The liquid mixture is distributed across an interior wall portion connecting the liquid inlet port and a liquid waste outlet port in the presence of the carrier gas (Block 830). For example, with reference to the fractional-volatilization separator 100 described above, a sample mixture may be introduced at the liquid inlet port 102, spread across the interior wall portion 108, and collected at the liquid waste outlet port 104. As described, the configuration of the interior wall portion 108 is designed to enhance evaporation of a first component part (e.g., a hydride and/or hydrogen gas) from a second component part of the sample mixture as a carrier gas flows from the carrier gas inlet port 116 to the carrier gas outlet port 118 across the mixture. The carrier gas and the first component part of the sample mixture are expelled at a carrier gas outlet port (Block 840). The liquid mixture is drained at a liquid waste outlet port after a first component part has been separated from a second component part of the liquid mixture and transferred to the carrier gas (Block 850).

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method comprising:
    receiving, at a first location, a sample to be analyzed by an Inductively Coupled Plasma (ICP) instrument, the Inductively Coupled Plasma (ICP) instrument employing a spray chamber and a torch, the spray chamber and the torch located downstream from the first location;
    initiating, proximate to the first location, a hydride generation reaction with the sample to form a hydride from the sample;
    introducing the hydride into the spray chamber with a carrier gas; and
    separately introducing hydrogen gas from a gas stream into the spray chamber or the torch to add the hydrogen gas to the hydride and the carrier gas, the spray chamber providing the hydride and the added hydrogen gas for analysis by the Inductively Coupled Plasma (ICP) instrument.

2. The method as recited in claim 1, wherein adding hydrogen gas from the gas stream to the hydride comprises introducing the hydrogen gas to a component part of the sample.

3. The method as recited in claim 1, wherein the ICP instrument comprises an axially-viewed ICP instrument.

4. The method as recited in claim 1, wherein the sample comprises a dry aerosol.

5. The method as recited in claim 1, wherein the sample comprises at least one of Arsenic, Manganese, Lead, Selenium, or Thallium.

6. The method as recited in claim 1, where adding hydrogen gas from the gas stream to the hydride comprises introducing the hydrogen gas to a center channel of the Inductively Coupled Plasma (ICP) instrument.

\* \* \* \* \*